United States Patent [19]

Beckmann

[11] 4,152,725

[45] May 1, 1979

[54] DISTORTION CORRECTING APPARATUS FOR LINE-SCANNING SYSTEM

[75] Inventor: Leo H. J. F. Beckmann, Delft, Netherlands

[73] Assignee: N.V. Optische Industrie "De Oude Delft", Netherlands

[21] Appl. No.: 855,163

[22] Filed: Nov. 28, 1977

[30] Foreign Application Priority Data

Dec. 3, 1976 [NL] Netherlands .......................... 7613491

[51] Int. Cl.$^2$ ......................... H04N 3/02; H04N 7/18
[52] U.S. Cl. .................................. 358/109; 358/199; 358/212
[58] Field of Search ............... 358/109, 199, 206, 212, 358/209, 285, 293

[56] References Cited

U.S. PATENT DOCUMENTS

| 3,078,340 | 2/1963 | Willey | 358/109 |
|---|---|---|---|
| 3,723,642 | 3/1973 | Laakmann | 358/212 |

Primary Examiner—Robert L. Griffin
Assistant Examiner—Joseph A. Orsino, Jr.
Attorney, Agent, or Firm—O'Brien and Marks

[57] ABSTRACT

A line scanning system wherein a multiple element detector array receives radiation from a scanning rotator having mirror surfaces inclined relative to the axis of rotation. Image distorting effects due to inequality of lines which are concurrently scanned, are offset by individually delaying the electric signals which are individually derived from the detector elements; these delays are related to the instantaneous scanning angle. The electrical signals, thus compensated are converted into a corresponding number of separate light beams which are individually applied to corresponding light inputs of a multiple input optical system comprising a configuration of prisms, which are effective to combine the separate input beams into a single output beam composed of coaxially disposed, rotationally symmetric sub-beams.

7 Claims, 3 Drawing Figures

DISTORTION CORRECTING APPARATUS FOR LINE-SCANNING SYSTEM

This invention relates to apparatus for scanning an area emitting a given kind of radiation, and for processing the radiation thus collected into a form suitable for reproduction or recording.

Apparatus of the kind to which this invention relates is described, for example, in U.S. Pat. No. 3,632,870 and comprises one or more surfaces reflecting the radiation, and which surfaces are rotatable about an axis of rotation; a configuration of detector elements with an array of n elements for simultaneously scanning n field lines transversely to said axis of rotation; and n light modulator units each responsive to an output signal derived from an associated one of said n detector elements. Such apparatus is generally used on board of aircraft for reconnaissance purposes.

In apparatus arranged in accordance with this prior art, the rotatable reflective surfaces, or mirrors, are parallel to the axis of rotation, a scanning beam and the beam to be deflected to an associated detector element being co-planar in a plane normal to the axis of rotation. A scanning beam moves along the radiant area at an angular velocity twice that of the axis of rotation. With an array of detector elements located so that its longitudinal direction is parallel to the direction of advance of the apparatus (the flight direction of the aircraft), the apparatus will scan the ground along a plurality of separate lines, the width of the strip being instantaneously viewed by the detector device increasing proportionally to the length of the scanning line, and hence proportionally to $1/\cos \phi$, $\phi$ being the instantaneous scanning angle, i.e., the angle between the scanning beam and the vertical. This means that when the scanning angle is increased, the field formed by the lines being scanned becomes wider, as a consequence of which the end portions of the strip traversed during one sweep may begin to overlap the end portions of a strip traversed during a next sweep. In order to avoid the consequential drawback of possible image blurring, in this prior technique, during the reproduction or recording of the collected image information, use is made of a system in which the lines traversed for reproduction or recording are matched in form to those along which the field is actually scanned. However, in this technique, only a relatively narrow strip of constant width of the line pattern is used for reproduction or recording. This means that as the scanning angle is increased the signals derived from the detector elements at the front and rear ends of an array will contribute to the reproduction to an increasingly lesser extent. When the scanning angle is 60° only half of the detector elements of such an array will contribute effectively. This accordingly degrades the quality of the reproduced or recorded image.

The problems inherent in this prior technique are not encountered, if the reflective surfaces of the scanner are at an angle, of preferably 45°, to the axis of rotation. For in that case the scanning beam is rotated by the scanning mirror, whereby the scan lines traversed by an array of detector elements are caused to remain parallel to each other. Such a rotated scanning beam, however, results in the scan lines being different in length, which detracts from this important advantage.

If, for example, the array of detector elements is arranged to extend vertically in its longitudinal direction, the detector elements, after reflection at the scanning mirror, will be projected vertically under the aircraft as a row of image elements which, at a zero angular position for the rotating 45% scanning mirror, extend parallel to the axis of rotation and also parallel to the flight direction, at least if it is assumed that the flight direction and the direction of axis of rotation of the scanning mirror are the same. Where, however, the scanning beam is rotated it is found that the projection of the row of image elements is distorted, while they also increase in size. As a result of such distortion, the area over which the aircraft flies will be scanned during each scan according to a plurality of parallel lines, corresponding to the number of detector elements making up the array, but the length of these scan lines will vary in dependence upon the scanning angle $\phi$. This means that an area covered during one scan by the array of detector elements has the form of a trapezium, which may cause image distortion during image reproduction or recording.

A possible solution for this problem is proposed in Dutch patent application No. 6812267, which was laid open to public inspection on Mar. 3, 1970. This proposal utilizes an optical method, and contemplates simulating the geometry of the projected field on the terrain. This prior technique has the drawback, however, that it is impossible to use large-aperture optics for the reproduction, which makes it necessary to use light sources of very high intensity.

The present invention provides a different solution, in which, on the one hand, the image distorting effect resulting from the inequality of the scan lines traversed is eliminated by an electrical means, and on the other hand, the isochronous image signals obtained from such elimination process are converted by optical means into a rotation-symmetrical beam configuration that can be combined with known per se large-aperture optics for reproduction or recording.

According to the present invention, there is provided apparatus for scanning an area emitting a given kind of radiation, and for processing the radiation thus collected into a form suitable for reproduction and recording, which comprises one or more surfaces reflecting the radiation, which surfaces are rotatable about an axis of rotation; a configuration of detector elements with an array of n elements for simultaneously reading n field lines transversely to said axis of rotation; and n light modulator units each responsive to an output signal derived from an associated one of said n detector elements, characterized in that each of said reflecting surfaces is at a fixed angle, of preferably 45°, to said axis of rotation; each of a plurality of the detector elements is coupled to a separate delay device serving to delay the signal from the associated detector element by a time interval varying with the scanning angle $\phi$ according to a pre-determined function, the arrangement being such that field elements located in a row parallel to said axis of rotation, are effective to produce isochronous signals at the respective outputs of the delay devices; and in that said light modulator units are optically coupled at their output end to prism means for combining the n separate beams of radiation generated by the n light modulator units, each of which light beams has been modulated with the appropriately delayed output signal from an associated one of said detector elements, to form a beam comprising n rotation-symmetrical component beams co-axially shifted together.

One embodiment of the invention will now be described, by way of example, with reference to the accompanying drawings. In said drawings, FIG. 1 is a diagram illustrating the image distortion arising in a scanner used in apparatus according to the present invention;

Figure 1:
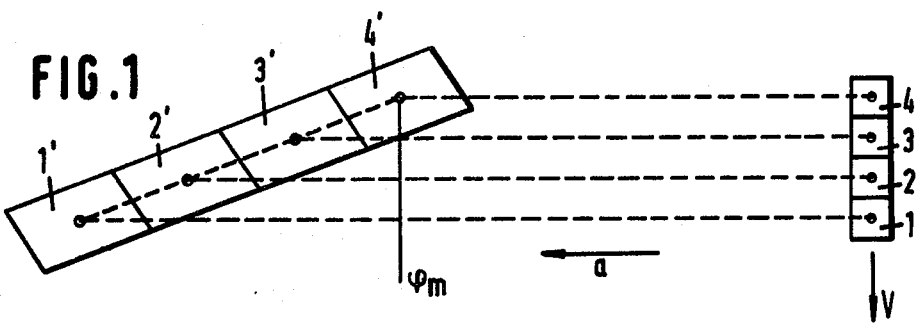

In the diagram of FIG. 1, the flight direction and the scanning direction are respectively designated by v and a. Designated by 1, 2, 3 and 4 are four image frames, or the projections of four detector elements arranged in a vertical array in opposition to a rotary scanning mirror disposed at an angle of 45° to its axis of rotation, which axis extends in the direction of flight. Frames 1, 2, 3 and 4 are formed when the scanning beam, or the scanning mirror, encloses a scanning angle $\phi$ of 0° with the vertical. When, using such a mirror, angle $\phi$ is increased the axes of the image frames will traverse mutually parallel lines over the field to be scanned. As angle $\phi$ increases, however, the scanning beams will also rotate about their own optical axis; it can be shown that such rotation corresponds to the rotation of the mirror. The row of image frames projected on the field to be scanned will be rotated, too, so that when angle $\phi$ has a given value a set of image frames will be projected on the field to be scanned as shown at 1', 2', 3' and 4'. The solution according to the present invention, whereby the image distorting effect resulting from such a rotation of the detector image is eliminated, will be best understood from a consideration of a line located in the field to be scanned, parallel to the flight direction. Each detector element of the array being considered will generate a signal at the moment when its image frame, such as 1, projected on the field being scanned will sweep across this line. This moment is different for each one of the array of detector elements under consideration. When the angular distance between two successive detector elements of the array is $\gamma$, it will be seen that the image frame projection of the first detector element will be advanced in the scanning direction relatively to the next element of the array under consideration by an angle $\Delta\phi = \gamma \cdot \sin\phi$. At a constant angular velocity $\omega$ of the axis of rotation, and hence of the scanning beam, we have the equation $\Delta\phi = \omega\Delta t$, in which $\Delta t$ is the time difference between the electrical signals derived from adjacent detector elements, generated when the projections of these detector elements reach the line under consideration. It is seen, therefore, that this time difference $\Delta t$ is proportional to sin $\phi$. The effect resulting from the rotation of the scanning beam can thus be eliminated according to the present invention by delaying the leading signal by a time interval varying proportionally to a given function, i.e. sin $\phi$. In a practical case, in which $\gamma = 1$ mrad and $\omega = 600$ rad. sec$^{-1}$, the signal from a detector element will have to be delayed relatively to the adjacent one in the array under consideration by an interval of up to approximately 0.83 $\mu$sec. When, for example, four detectors are used in an array, the maximum delay to be introduced will be given by $3 \times 0.83 = 2.5 \mu$usec., introducing a lead on one scanning side, and a lag between the signals on the other. When, however, a fixed delay is added to the delayed signals in all instances, it is possible to operate with lagging signals throughout the full scan area. These delay periods are small relatively to the time required for one scan, which for example is of the order of 3.3 milliseconds.

FIG. 1 also shows, in dotted lines, that the strip of terrain covered by the detector elements during a scan is in principle trapezoidal in shape, so that during successive sweeps a pattern of trapezoidal strips is scanned. This means that, without the employment of distortion-eliminating means, a line parallel to the direction of flight will be depicted as a serrated line.

Figure 2:
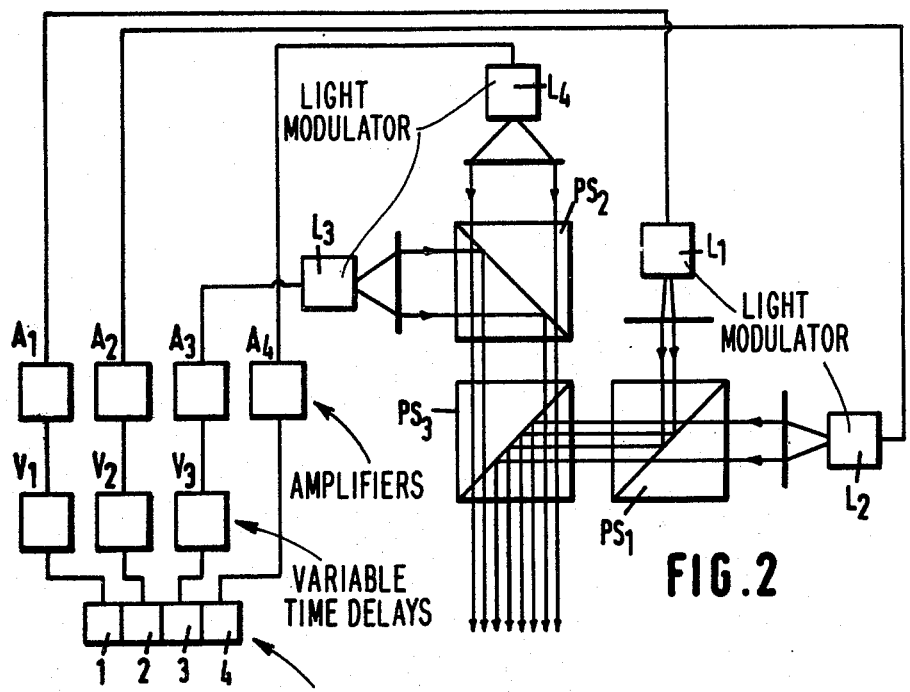
FIG. 2 is a diagram showing an embodiment of the present invention.

FIG. 2 shows a diagram of one embodiment of the present invention. As shown, there are four detector elements 1–4, disposed according to a vertical array and opposite a scanner (not shown) rotatable about an axis and comprising, for example, three mirrors each enclosing a fixed angle of 45° with the axis of rotation. According to the invention, each of these detector elements, except for the last, is coupled to a separate delay device $V_1$ to $V_3$. Each of these delay devices is arranged to delay the electrical signal received from the associated detector element by a time interval varying during a scan according to a pre-determined function of the scanning angle $\phi$. If the time difference $\Delta t$ between the signals from adjacent detector elements, such as 1 and 2, is given by $\gamma/\omega \cdot \sin\phi$, the delay device $V_1$, associated with the first detector element 1 must always introduce a delay of $3 \cdot \Delta t = 3\gamma/\omega \cdot \sin\phi$, while the next delay devices have to introduce a delay of $2 \cdot \Delta t$ and $\Delta t$ respectively. With such an organization, only those signals which correspond to a central, rectangular portion, determined by a given maximum angle $\phi$, of a trapezoidal field strip, as obtained each time when during a scan the projections of the detector elements are swept over the terrain, will be processed further and effectively used in the reproduction or recording. When the electrical signals from the detector elements have been delayed in the manner described above there are in effect formed isochronous signals representative of an image geometry corresponding to the geometry on the area scanned, in other words, a given distance ratio in this area is also represented by the electrical signals thus delayed. That is to say, the thus delayed signals can be regarded as signals obtained when the scanner has scanned a number of parallel and equally long lines of the area covered.

The signals can be delayed in the desired manner using analogue shift registers, preferably in the form of charge coupled devices, in which a signal presented at the input is stored in the form of a proportional amount of electrical charge in a respective semi-conductive region. In response to a control signal applied to such a shift register, the charge thus stored can be shifted to an adjacent region of the shift register. It is accordingly possible to form an analogue shift register with n stages, each stage being capable of introducing an incremental delay of $\Delta t$. If the control signal for shifting the stored information has a frequency f, i.e. the period T of the control signal equals 1/f, than after completion of n cycles or excursions of the control signal, a signal presented to a delay device will have been shifted through n stages, whereby it has been delayed by a time interval of $n \cdot \Delta t$. If the period T is selected to equal the incremental delay interval $\Delta t$, the delay introduced by a delay device will be given by n/f. It is thus possible to achieve the desired scan angle-depedent delay for the signals by causing the frequency f to vary in the desired manner according to a sinusoidal function in dependence on the scanning angle $\phi$.

Figure 3:
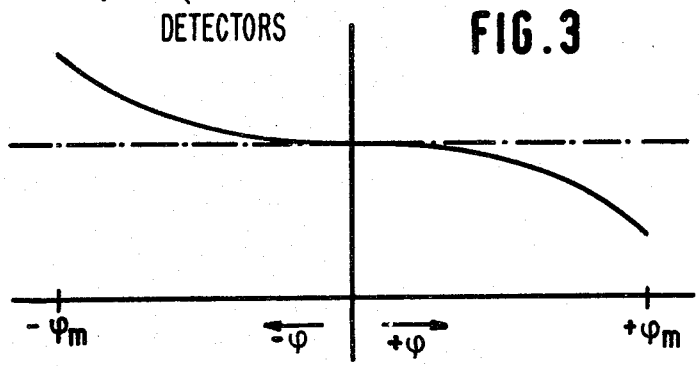
FIG. 3 is a diagram showing the configuration of the frequency of a control signal as a function of the scanning angle.

FIG. 3 diagrammatically shows how the frequency of the control signal varies as a function of the scanning angle $\phi$. With such a frequency dependent relation, the delay introduced will exhibit at the maximum angle $\phi_m$ the longest difference from $\phi=0$ (vertically under the airplane) required for that threshold angle. It is thus possible to cause the delay to vary in dependence on the scanning angle according to a sinusoidal function.

The signals from the detector elements, thus delayed in the desired manner, are supplied via processing means such as amplifiers $A_1$–$A_4$ to a plurality of light modulator units $L_1$–$L_4$. These light modulator units can generate a plurality of separate light beams, each of which is modulated in brightness with the signal from the associated detector element.

According to a further aspect of the present invention, these light modulator units $L_1$–$L_4$ are optically coupled to a prism unit, comprising, in the embodiment shown, three prism sub-units $PS_1$, $PS_2$ and $PS_3$. Each of these sub-units comprises a pair of prisms cemented together at their oblique faces. A reflective layer Z of suitable, i.e. elliptic, shape is provided in this boundary surface of the prisms thus cemented together. It is thus possible, by means of such a sub-unit, for two separate light beams, such as from two light modulator units, to be, as it were, concentrically combined, the two light beams being co-axially shifted one into the other to form a rotation-symmetrical beam composed of two component beams. By disposing the sub-units as shown diagrammatically in FIG. 2 and providing them with suitable reflective layers on the boundary faces, it is possible to combine the four separate light beams referred to in this example, in the manner described above, to form a single composite light beam suitable to be supplied to a known per se reproducing apparatus equipped with large-aperture optics and with facilities for controlling the light spot active for reproduction or recording in dependence on the film speed, using the well-known principle of slit control for the overall dimension of the imaging slit. The light modulators $L_1$–$L_4$ and the prism sub-units $PS_1$–$PS_3$ should be arranged in such interrelationship that the light beams from the light modulators pass along equally long transmission paths having substantially identical transmission characteristics and extending to the output end of the prism sub-unit serving as the output sub-unit, such as $PS_3$.

I claim:

1. Apparatus for scanning an area emitting a given kind of radiation, and for processing the radiation thus collected into a form suitable for reproduction and recording, which comprises one or more surfaces reflecting the radiation, which surfaces are rotatable about an axis of rotation; a configuration of detector elements with an array of n elements for simultaneously scanning n field lines transversely to said axis of rotation; and n light modular units each responsive to an output signal derived from an associated one of said n detector elements; and characterized in that each of said reflecting surfaces is at a fixed angle, of preferably 45°, to said axis of rotation; each of a plurality of the detector elements is coupled to a separate delay device serving to delay the signal from the associated detector element by a time interval varying with the scanning angle $\phi$ according to a pre-determined function, said delay devices being such that radiations from points in the scanned area located in rows parallel to said axis of rotation and horizontally spaced from a vertical line through the apparatus, are effective to produce isochronous signals at the respective outputs of the delay devices; and in that said light modulator units are optically coupled at their output ends to prism means for combining the n separate beams of radiation generated by the n light modulator units, each of which light beams has been modulated with the appropriately delayed output signal from an associated one of said detector elements, to form a beam comprising n rotation-symmetrical component beams co-axially shifted together.

2. Apparatus according to claim 1, wherein a delay device is formed as a shift register arranged to cooperate with means for varying the shift frequency at a periodicity corresponding to the scan rate and in inversely proportional relationship to the scanning angle $\phi$.

3. Apparatus according to claim 2, wherein a shift register is formed as a charge-coupled device, the number of stages of which is determined by the sequential number of the associated detector element in said array.

4. Apparatus according to claim 1 wherein the prism unit comprises n−1 sub-units, each comprising a pair of triangular prisms cemented together at their oblique faces, with a reflective layer being applied at the boundary face, the form of said layer being suited to the component beams to be combined.

5. Apparatus according to claim 4, wherein the light modulators and said sub-units of the prism unit are arranged in such interrelationship that the light beams from the light modulators pass along equally long transmission paths to the output face of the prism sub-unit serving as the output sub-unit of said prism unit.

6. Apparatus according to claim 2 wherein the prism unit comprises n−1 sub-units, each comprising a pair of triangular prisms cemented together at their oblique faces, with a reflective layer being applied at the boundary face, the form of said layer being suited to the component beams to be combined.

7. Apparatus according to claim 3 wherein the prism unit comprises n−1 sub-units, each comprising a pair of triangular prism cemented together at their oblique faces, with a reflective layer applied at the boundary face, the form of said layer being suited to the component beams to be combined.

* * * * *